United States Patent
Cise et al.

(10) Patent No.: US 6,688,306 B1
(45) Date of Patent: Feb. 10, 2004

(54) CLAMPING ASSEMBLY FOR MAINTAINING THE POSITION OF A RESPIRATORY CARE TREATMENT DEVICE

(75) Inventors: David M. Cise, Herriman, UT (US); Steven M. Wood, West Jordan, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/723,314

(22) Filed: Nov. 27, 2000

(51) Int. Cl.$^7$ ............................................... A62B 9/04
(52) U.S. Cl. ........................ 128/202.27; 128/200.26; 128/207.14
(58) Field of Search .................. 128/200.26, 202.27, 128/204.11, 204.12, 206.27, 207.14

(56) References Cited

U.S. PATENT DOCUMENTS

| | | | |
|---|---|---|---|
| 3,774,616 A | * 11/1973 | White et al. | 128/200.26 |
| 3,991,762 A | * 11/1976 | Radford | 128/200.26 |
| 4,270,529 A | * 6/1981 | Muto | 128/200.26 |
| 4,340,046 A | * 7/1982 | Cox | 128/200.26 |
| 4,573,965 A | 3/1986 | Russo | |
| 4,978,341 A | * 12/1990 | Niederhauser | 604/256 |
| 5,083,561 A | 1/1992 | Russo | |
| 5,097,827 A | * 3/1992 | Izumi | 128/200.26 |
| 5,135,490 A | 8/1992 | Strickland | |
| 5,158,553 A | * 10/1992 | Berry et al. | 604/248 |
| 5,158,569 A | 10/1992 | Strickland et al. | |
| 5,220,916 A | 6/1993 | Russo | |
| 5,255,676 A | 10/1993 | Russo | |
| 5,306,272 A | 4/1994 | Cohen et al. | |
| 5,324,271 A | * 6/1994 | Abiuso et al. | 604/167.03 |
| 5,338,314 A | 8/1994 | Ryan | |
| 5,464,011 A | * 11/1995 | Bridge | 128/200.26 |
| 5,582,161 A | 12/1996 | Kee | |
| 5,676,136 A | 10/1997 | Russo | |
| 5,775,325 A | 7/1998 | Russo | |
| 5,895,376 A | * 4/1999 | Schwartz et al. | 604/256 |
| 5,935,112 A | * 8/1999 | Stevens et al. | 604/256 |
| 6,086,529 A | 7/2000 | Arndt | |
| 6,109,259 A | * 8/2000 | Fitzgerald | 128/200.26 |
| 6,109,264 A | * 8/2000 | Sauer | 128/200.26 |
| 6,165,168 A | 12/2000 | Russo | |
| 6,221,057 B1 | * 4/2001 | Schwartz et al. | 604/246 |
| 6,331,176 B1 | * 12/2001 | Becker et al. | 604/533 |

FOREIGN PATENT DOCUMENTS

WO    9815310    4/1998

OTHER PUBLICATIONS

EPO Search Report Aug. 28, 2002.
U.S. patent application No. 29/133,260, filed Nov. 27, 2000 (BAL–92–D).
U.S. patent application No. 29/133,261, filed Nov. 27, 2000 (BAL–93–D).
U.S. patent application No. 29/133,262, filed Nov. 27, 2000 (BAL–94–D).
International Preliminary Examining Authority/U.S., PCT Written Opinion (PCT Rule 66), International Patent Application No. PCT/US01/44372, International Filing Date Nov. 27, 2001, Date of Mailing Jul. 10, 2003.

* cited by examiner

Primary Examiner—Weilun Lo
Assistant Examiner—Michael Mendoza
(74) Attorney, Agent, or Firm—Dority & Manning, P.A.

(57) ABSTRACT

A medical device clamping assembly includes proximal and distal axially aligned members. The proximal and distal members are movable relative to each other. A channel is defined through the members for receipt of a treatment device, such as a catheter tube, therethrough. A clamping member is configured between the proximal and distal members and defines a portion of the channel. The clamping member is actuated between an unclamped configuration and a clamped configuration by a clinician moving one of the distal or proximal members relative to the other. In its clamped position, the clamping member clamps upon and prevents axial movement of the medical treatment device through the clamping assembly.

23 Claims, 5 Drawing Sheets

CLAMPING ASSEMBLY FOR MAINTAINING THE POSITION OF A RESPIRATORY CARE TREATMENT DEVICE

FIELD OF THE INVENTION

The present invention relates generally to the field of respiratory care systems for intubated patients.

BACKGROUND

Proper long-term respiratory care of intubated patients requires that multiple medical procedures be performed on the patient. Such procedures may include, for example, ventilation of the patient's lungs; aspiration of secretions from the lungs; oxygenation of the lungs; elimination or reduction of residual $CO_2$ from the lungs; visual inspection of portions of the respiratory system; sampling sputum and gases; sensing parameters such as flow rates, pressure, and temperature of gases within the respiratory system; and/or the administration of medication, gases, and/or lavage.

In the majority of these procedures, a medical treatment device, such as a catheter assembly, is connected to a patient's artificial airway, for example a tracheostomy tube or endotracheal tube. A connecting member, such as an adapter, manifold or other like member, may be attached to the proximal end of the artificial airway and the medical treatment device is inserted through the adapter or manifold and into the artificial airway. The manifold may include a variety of ports through which any manner of medical treatment device may be inserted into the patient's respiratory system for carrying out any combination of the procedures mentioned above.

During certain procedures, it is important that the medical treatment device be precisely positioned in the patient's respiratory system. For example, when using a gas insufflation catheter to oxygenate a patient's lungs, it is necessary to precisely position the catheter at the carina of the lung and maintain that catheter in that position. Similarly, it may be necessary to precisely place a biopsy device, sampling device, or monitoring device into the patient's respiratory system and maintain the positioning of the device for the duration of the procedure.

One concern with current medical devices is that it is difficult to ensure that such devices are held in position within the patient's respiratory system when inserted through the artificial airway. This is particularly the case when different procedures must be performed simultaneously through the artificial airway requiring at least one medical treatment device to be maintained in position while another medical procedure is conducted with a second medical treatment device. The present invention provides a reliable and relatively easy to use clamping assembly for establishing and maintaining the position of a medical treatment device inserted through a patient's artificial airway.

SUMMARY OF THE INVENTION

Objects and advantages of the invention will be set forth in part in the following description, or may be obvious from the description, or may be learned through practice of the invention.

As used herein, the phrase "artificial airway" includes devices such as tracheostomy tubes, endotracheal tubes, and the like, that define an artificial ventilation path into a patient's respiratory system. The present invention is not limited to use with any particular type of artificial airway.

The present invention is directed generally to a respiratory care assembly particularly suited for use with a ventilating system. In particular, the invention relates to a unique clamping assembly incorporated in the respiratory care assembly. The clamping assembly provides the clinician with a reliable and effective assembly for maintaining the position of a medical treatment device that has been inserted through an artificial airway and into a patient's respiratory system. The clamping assembly holds the medical treatment device in its position in the respiratory system until released by the clinician.

The clamping assembly includes first and second axially aligned members. These members may be considered as "proximal" and "distal" members depending upon their orientation in the respiratory system. At least one of the first and second members is movable relative to the other respective member. An axial channel is defined through the first and second members and is configured for axial sliding receipt of a medical treatment device, such as a catheter tube of any manner of catheter assembly.

A clamping member is disposed in-line with the first and second axially aligned members. The clamping member defines at least a section or portion of the channel through which the medical treatment device passes. The clamping member has an un-clamped configuration wherein the treatment device is slidable through the channel, and a clamping configuration wherein the clamping member clamps upon and prevents axial movement of the medical treatment device through the channel. The clamping member is operably connected to each of the first and second members so that relative movement between the members actuates the clamping device.

The first and second members may be threadedly engaged such that threaded rotation of one member results in relative axial displacement between the members. In this embodiment, the clamping member may be a compressible annular sleeve member having opposite axial ends that are connected with the first and second members, respectively. A treatment device, such as a catheter tube, passes through the annular sleeve member. The annular sleeve member is disposed in a restraining recess such that upon relative axial movement of the first and second members, the annular sleeve is compressed axially. Because the sleeve is restrained in a fixed diameter recess, radial expansion of the sleeve resulting from its axial compression is directed radially inward resulting in reduction of the inner diameter of the annular sleeve thereby causing the sleeve to clamp upon the treatment device disposed therethrough. To release the treatment device, the clinician simply moves the first and second members in the opposite direction. For example, if the first and second members are threadedly engaged, the clinician rotates the movable member in the opposite direction to release the treatment device.

The first and second members include connecting or mating members at their respective ends so that the clamping assembly may be connected permanently or removably in-line in a respiratory system. For example, the proximal member may include a connecting member configured for permanent or removable engagement with the distal end of a catheter assembly. Similarly, the distal member may include a connecting member configured for connection to a patient's artificial airway. It should be understood that connection of the assembly to an artificial airway may be accomplished through an intervening mechanism, such as a manifold having one or more ports to which the distal member is connectable. For simplicity and ease of connection, the distal connecting member may be a distal extension configured to be pressed into a receiving port of the manifold.

To aid the clinician in operation of the clamping assembly, it may be desired to incorporate a gripping member on the movable or rotatable member. The gripping member may be, for example, a grip ring having a plurality of grip enhancing protrusions, or the like. The grip ring may define a maximum outer diameter of the respective proximal or distal member.

In one embodiment of the clamping assembly, the proximal member is the movable member and the distal member is held stationary relative to the patient's artificial airway. It should be appreciated that this is but one working embodiment. It is just as feasible for the distal member to be rotatable or movable, or for both members to be independently rotatable or movable.

It should also be appreciated that the clamping member need not necessarily be actuated by axial movement between the proximal and distal members. For example, it is within the level of those skilled in the art to configure a clamping member that operates with a pure rotational or twisting motion. The axially compressible annular sleeve discussed herein is but one embodiment of a clamping member that works particularly well with threaded axial displacement between the first and second members. The present invention is not, however, limited to a compressible annular sleeve clamping member.

It should be appreciated that the clamping assembly according to the invention is not limited in its application or use with any particular medical treatment device. The clamping sleeve and axial channels defined through the first and second members may be sized and configured to accommodate any manner of conduit, tube, or the like, depending on the medical procedure and appropriate medical device. In this description, the medical device is a catheter assembly having a catheter tube that is slidable through the clamping assembly. It should be appreciated that this is merely one embodiment of the invention and is presented for purposes of explaining the invention.

The present invention is also drawn to any manner of a respiratory care assembly incorporating the novel clamping assembly described herein. A respiratory care assembly according to the invention utilizes the clamping assembly to introduce any manner of medical treatment device, such as a catheter assembly, through a patient's artificial airway. The particular type of medical treatment device is dictated by the desired medical procedure. For example, in a procedure wherein it is desired to aspirate secretions from a patient's lungs, the respiratory care assembly may include a suction catheter assembly incorporating a clamping assembly of the present invention. The suction catheter assembly includes a catheter tube that is slidable through the axial channel defined in the clamping assembly and through the patient's artificial airway to a desired position or location in the respiratory tract for suctioning secretions from the patient's lungs. Once the catheter has been properly placed by the clinician, it is a relatively simple procedure for the clinician to rotate or move the proximal member of the clamping assembly to securely lock the catheter in its axial position.

In another example, a gas insufflation catheter may be required to oxygenate a patient's lungs. The insufflation catheter utilizes a catheter tube positioned at the cornea of the lung to administer oxygen directly into the lung. Once the clinician has properly positioned the catheter at the cornea of the lung, the catheter is axially locked in this position by the clinician simply rotating the proximal member. The catheter is securely held in position until the clinician rotates the proximal member in the opposite direction and withdraws the catheter.

It should thus be appreciated that the invention is not limited to any particular type of medical treatment device or medical procedure, but is useful in any application wherein it is desired to securely position and hold a medical treatment device in a desired position within the patient's respiratory system.

The invention will be explained in further detail below with reference to a particular embodiment illustrated in the figures.

DETAILED DESCRIPTION

Reference will now be made in detail to examples and embodiments of the invention. Each example is provided by way of explanation of the invention, and not meant as a limitation of the invention. For example, features illustrated or described as part of one embodiment can be used with another embodiment to yield a still further embodiment. It is intended that the present invention include such modifications and variations not particularly described herein.

In the drawings, each embodiment is arranged such that the distal direction (referring generally to the direction closer to the patient) is located at the bottom of the figure while the proximal direction (generally referring to the direction closer to the clinician) is located at the top of the figure.

Figure 5:
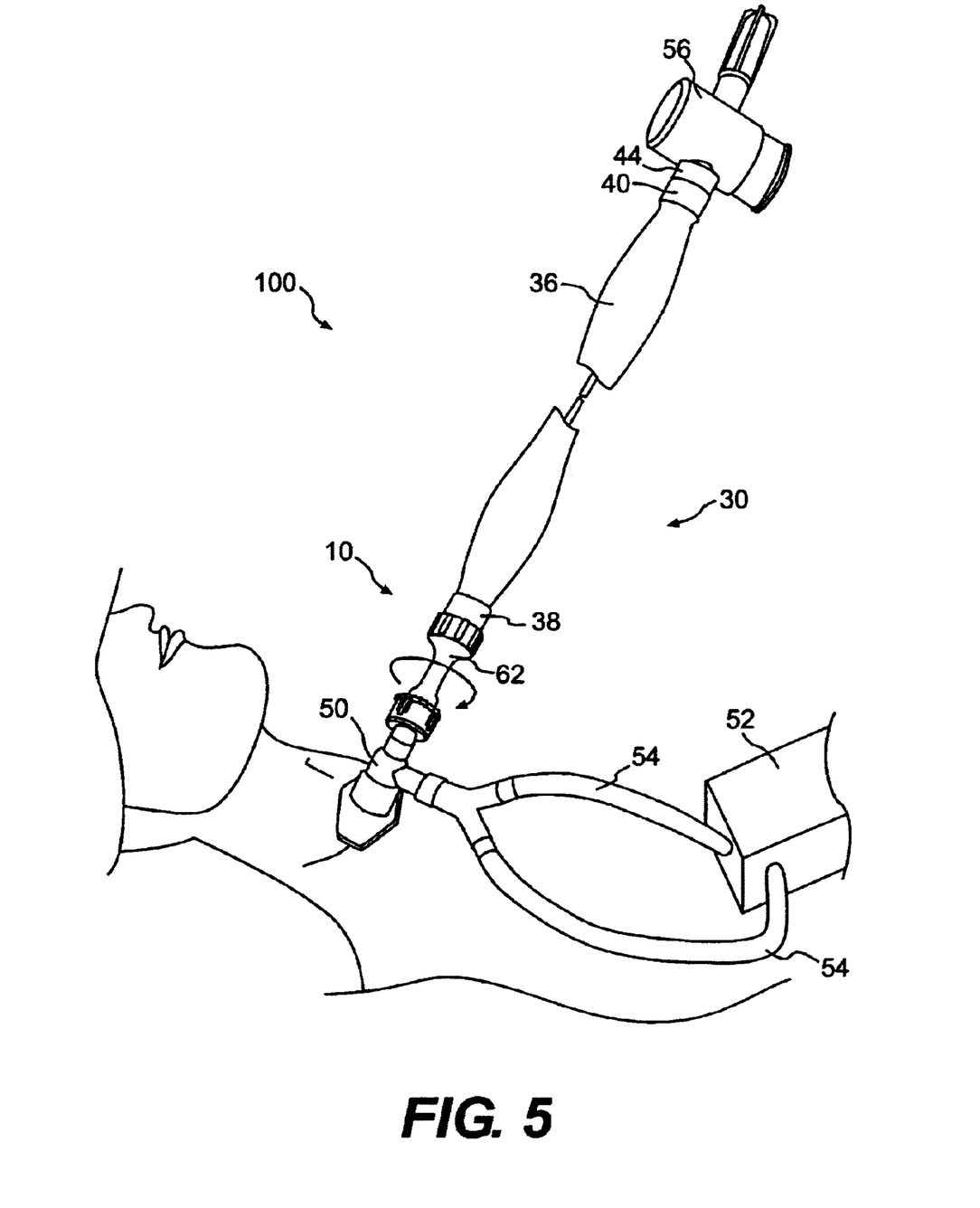
FIG. 5 is a perspective view of a respiratory care assembly according to the present invention.

An embodiment of a clamping assembly according to the present invention is illustrated generally at 10 in the figures. The assembly 10 is particularly configured for use in a respiratory care assembly which is adapted to insert a medical treatment device, such as a catheter tube, into a patient's respiratory system through an artificial airway. In some instances, an airway connector, such as the manifold 50 shown in FIG. 5 is connected to the patient's artificial airway. The airway connector may have various configurations but will include at least one port to which the assembly 10 may be connected.

Figure 1:
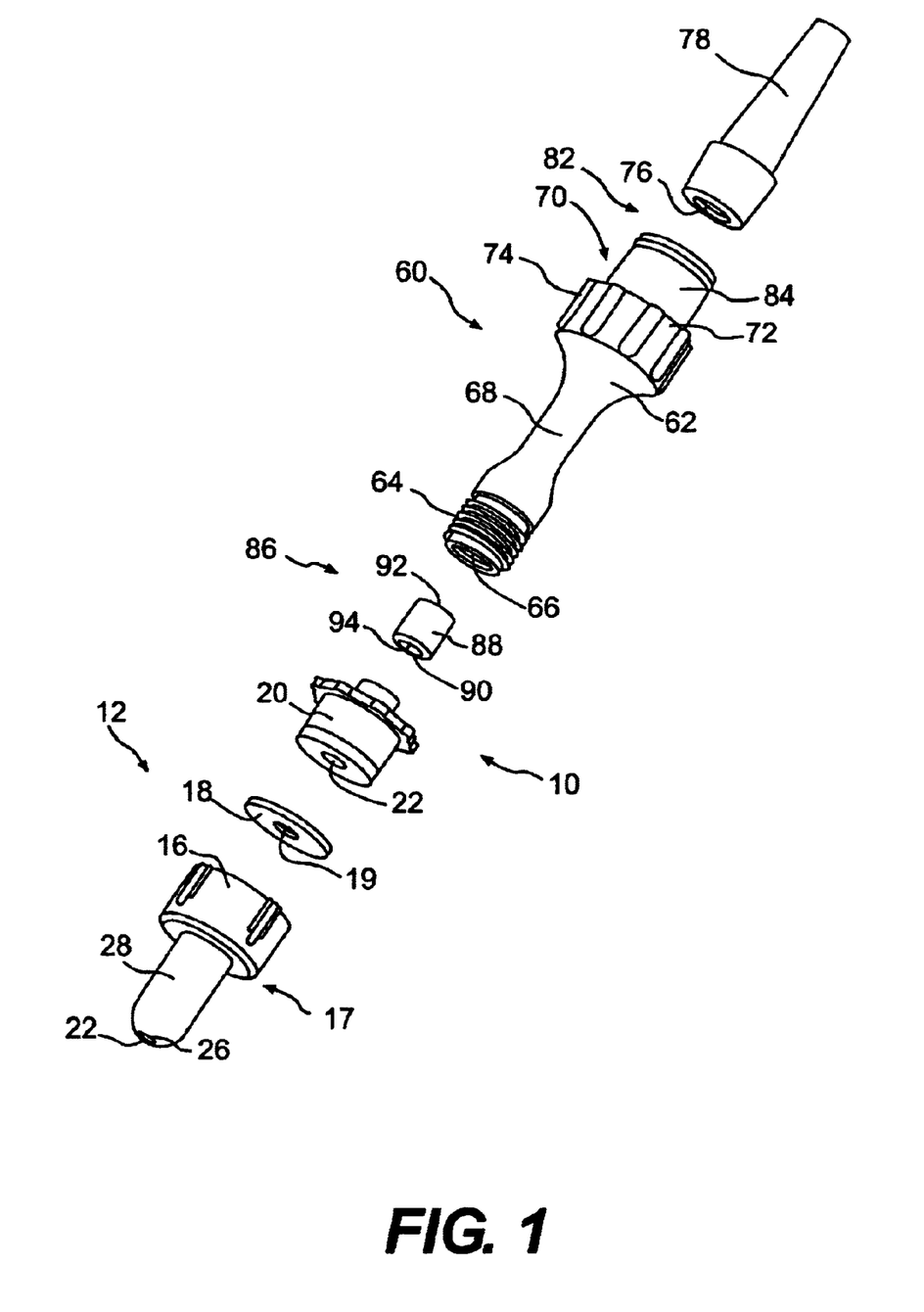
FIG. 1 is an exploded component view of an embodiment of the clamping assembly according to the present invention.
Figure 2:
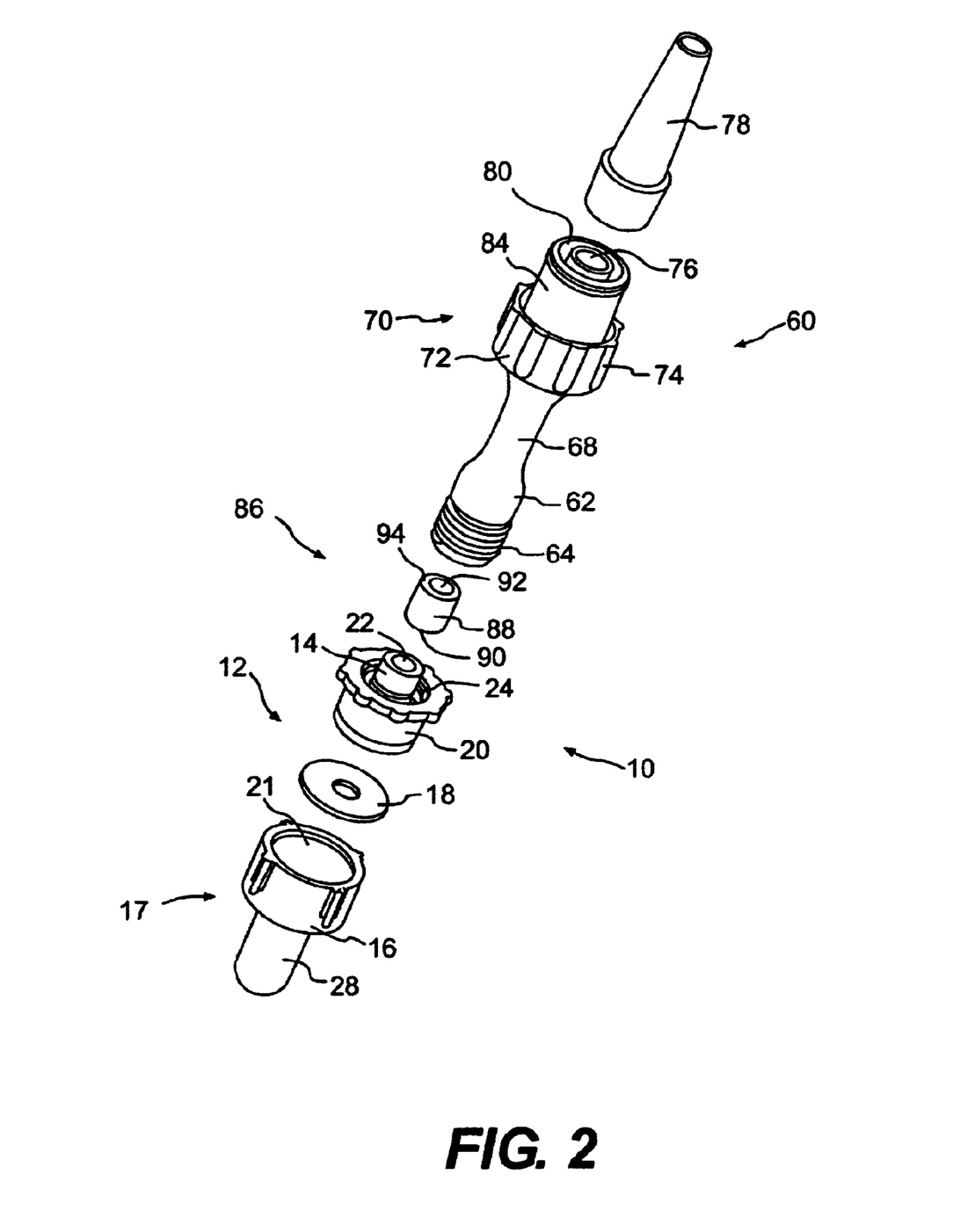
FIG. 2 is an alternate exploded component view of the clamping assembly.

Referring to FIGS. 1 and 2 in particular, the clamping assembly 10 according to the present invention includes a first or distal member 12, and a second or proximal member 60. In the embodiment illustrated in FIGS. 1 and 2, the first or distal member 12 includes an end portion 17, a seal 18 and an insert 20. The end portion 17 may include, in selected embodiments, a base member 16 and a connecting member 28. In certain embodiments, the connecting member 28 and the base 16 may be formed as a single piece such as, for example, by injection molding.

The connecting member 28 of the end portion 17 connects the clamping assembly 10 to the artificial airway. The connecting member 28 may be press-fit into the artificial airway or the manifold 50, or another connector disposed between the artificial airway and the connecting member 28.

In the embodiment depicted in FIGS. 1 and 2, the base member includes an internal recess 21. The distal portion of the insert 20 may be inserted into the recess 21 of the base member 16. A seal 18 having a hole 19 may be disposed between the insert 20 and the base member 16 within the recess 21. The seal serves to scrape mucous and other secretions from the surface of a catheter tube 34 withdrawn therethrough, as explained in greater detail below. The insert 20 may also be otherwise engaged to the base member 16.

The insert 20 may also include, in particular embodiments, a threaded inner diameter portion 24 which is best shown in FIG. 2.

The first or distal member 12 also includes a channel 22 which extends axially through the end portion 17, the hole 19 and the insert 20. The distal most point 26 of the axial channel 22 is located at the end of the connecting member 28.

The proximal member 60, as shown in the illustrated embodiments, includes an elongated base member 62 which includes a restraining recess 66, a threaded outer diameter portion 64, a grip enhancing member 70, an elongated shaft 68 and a medical device connector 82. The restraining recess 66 is defined in the distal end of the base member 62. The threaded outer diameter portion 64 is adapted to engage the threaded inner diameter portion 24 of the distal member 12.

To aid the clinician in manipulation of the proximal or second member 60, it may be desired to provide a grip enhancing member 70 on an exterior surface of the proximal member 60. For example, in FIG. 1, the grip enhancing member 70 includes a radially extending gripping ring 72 which includes a plurality of protrusions 74 disposed therearound. The outermost diameter of the ring 72 may be selected so that the gripping ring does not interfere with the operation of the medical device by the clinician. The gripping ring 72 may be variously positioned on the clamping assembly 10. For example, an elongated shaft 68 may be disposed between the threaded distal end 64 and the gripping ring 72. By moving the gripping ring 72 away from patient's artificial airway and closer to the clinician, the clinician is provided with adequate space to actuate and adjust the clamping assembly 10.

Figure 3:
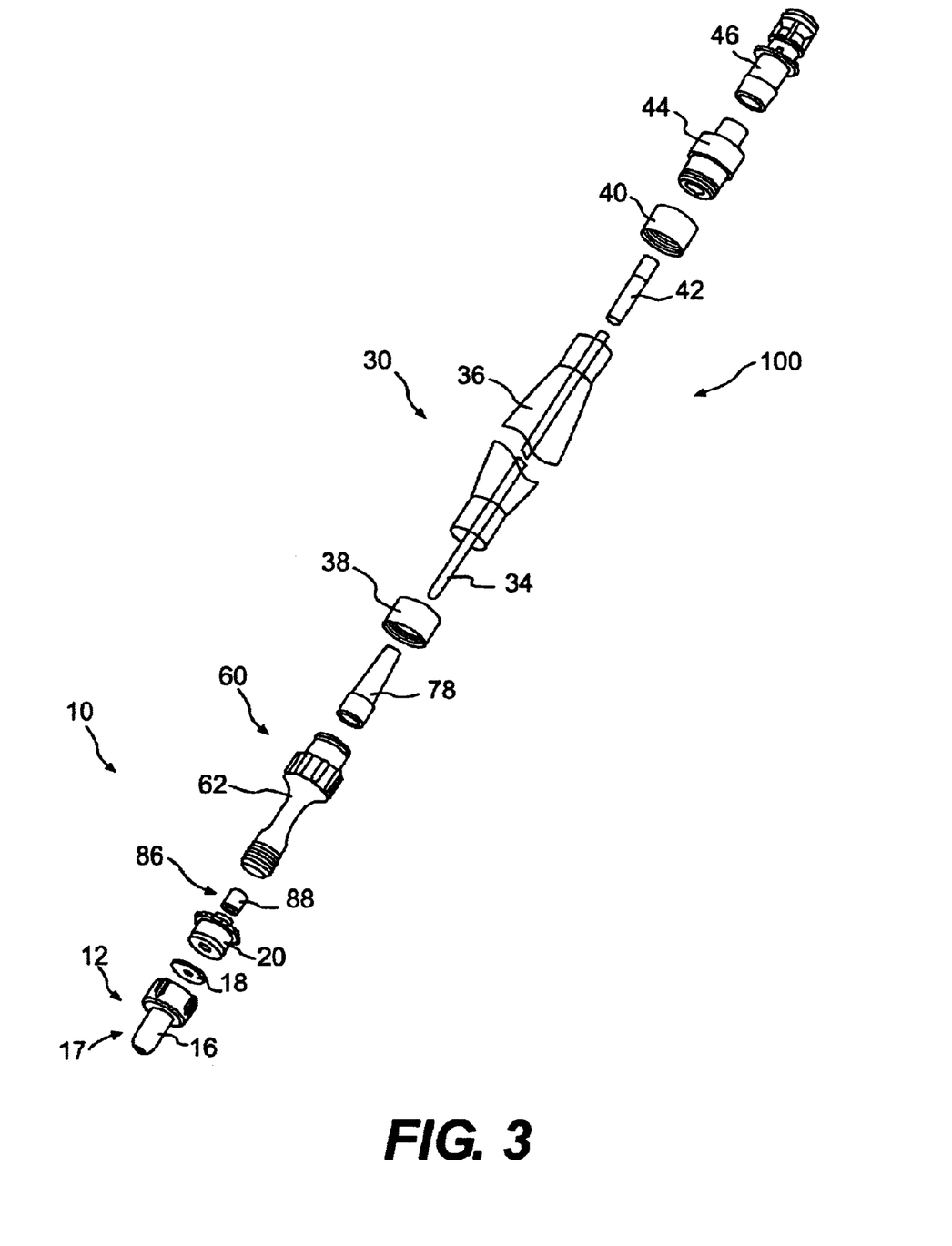
FIG. 3 is a perspective exploded view of the clamping assembly and a catheter assembly.
Figure 4:
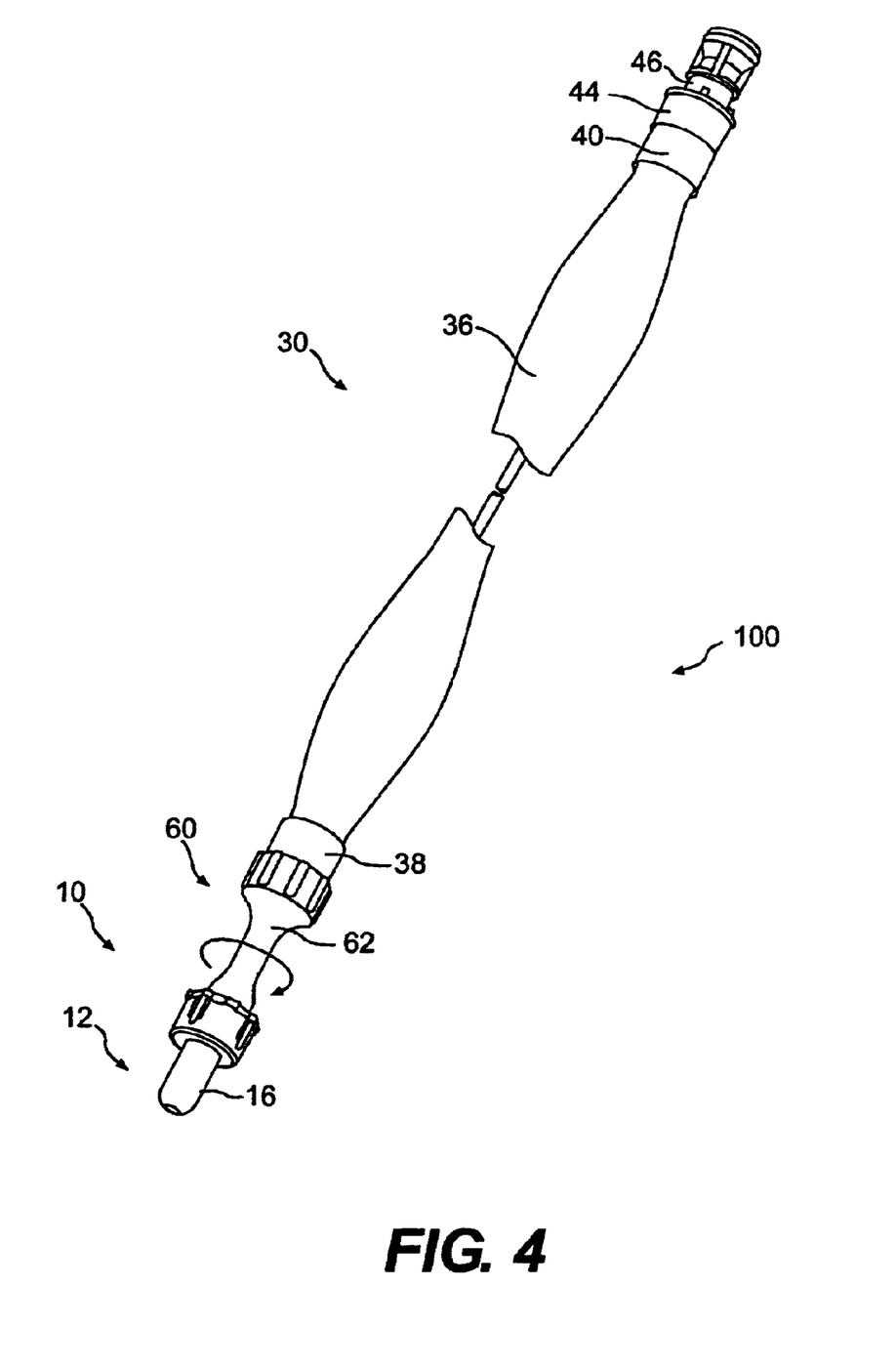
FIG. 4 is a perspective view of the assembly illustrated in FIG. 3.

The proximal member 60 also includes a medical device connector 82, for permanently or removably connecting the proximal member 60 to any manner of medical treatment device, such as, for example, a catheter assembly 30 (FIGS. 3–5). In the embodiment illustrated in the figures, clamping assembly 10 is permanently attached to the catheter assembly 30. A cylindrical proximally extending portion 84 of the base 62 is provided for engagement with a distal engaging ring 38 of the catheter assembly 30 (FIGS. 3–5). As with the connecting member of the distal member 12, it should be appreciated that any manner or configuration of connecting device may be utilized to connect the proximal member to any manner of treatment device.

It should be appreciated that the distal and proximal members 12, 60 are not limited by their shape and configuration.

The distal and proximal members 12 and 60, respectively, are axially aligned so that their respective axial channels form a continuous axially extending channel through the aligned components. This channel is appropriately sized to receive a medical treatment device, such as a catheter tube. In an unclamped configuration of the clamping assembly 10, the catheter tube or other treatment device is able to axially slide through the assembly 10 and into the respiratory tract of an intubated patient.

For purposes of discussion, a catheter will be used as an exemplary medical treatment device. It should, however, be appreciated, that the present invention is not limited to use with a catheter, but may be used in any application wherein it is desired to axially position and hold a variety of medical devices, in position in the patient's respiratory tract.

The distal and proximal members 12, 60 are configured so that there is relative movement between the members. In the illustrated embodiment, this relative movement is in an axial direction and may be accomplished by threaded engagement between the members.

Referring particularly to FIGS. 1 and 2, a clamping member is positioned between the first or distal member 12 and the second or proximal member 60. The clamping member is actuated by the relative movement between the distal and proximal members 12 and 60, respectively. For example, in the illustrated embodiment the clamping member includes a compressible annular sleeve 88 having a channel 94 defined therethrough. The channel 94 is in axial alignment with the channels 22 and 76 that are defined through the distal and proximal members 12 and 60, respectively, and thus forms at least a portion of the axial channel through which the catheter tube passes. The clamping member 86 has an un-clamped configuration wherein the catheter tube is freely slidable through the assembly 10, and a clamping position wherein the clamping member 86 clamps upon and prevents relative axial movement of the catheter tube through the assembly 10, as described in greater detail below.

The annular sleeve embodiment of the clamping member operates similar to a conventional Touhy-Borst seal available from Micor, Inc. The Touhy-Borst devices have been used for various purposes in the medical industry and are well known by those skilled in the art.

The compressible annular sleeve 88 is disposed so that its proximal end 92 is contacted by the proximal member 60 and its distal end 90 is contacted by the distal member 12. For example, referring to FIGS. 1 and 2, the annular sleeve 88 is disposed in a closed-end recess 66 defined in the distal end of proximal member 60. This recess has a fixed diameter slightly greater than the outer diameter of the sleeve 88. Referring to FIG. 2, an axial protrusion 14 of distal member 12 abuts against the distal end 90 of the annular sleeve 88. Upon rotation of the proximal member 60 in a tightening direction, the proximal member 60 is drawn towards the stationary distal member 12. This results in axial compression of the annular sleeve 88 within the recess 66. This axial compression results in a radial expansion of the annular sleeve. However, because the sleeve is restrained or restricted within the fixed diameter recess 66, the radial expansion is directed radially inward causing the inner diameter of the annular sleeve 88 to compress or reduce. This reduction of the inner diameter results in the annular sleeve 88 securely clamping upon a catheter tube disposed therethrough.

Thus, in an un-clamped configuration of the assembly 10, a clinician can easily slide a catheter tube or like device through the assembly 10 and into the patient's respiratory tract to a desired axial location. In order to lock the catheter tube at this position, the clinician simply rotates the proximal member 60 in a tightening direction causing the clamping member 86 to clamp upon the catheter tube. The catheter tube is prevented from further axial movement within the assembly 10 until the clinician rotates the proximal member 60 in the opposite direction. At this point, the catheter tube can be freely withdrawn from the patient.

As in the illustrated embodiment, it may also be desired to provide a relatively flexible and proximally extending strain relief member 78 at the end of the proximal member 60. The catheter tube passes through the stain relief member 78 which prevents the catheter tube from kinking or catching on the edge of the base member 62. The strain relief member 78 also aids the clinician in threading the catheter tube through the clamping assembly 10. Referring particularly to FIG. 2, the stain relief member 78 is press-fitted or adhered into an annular groove 80 defined in the proximal end of the base member 62.

FIGS. 3 through 5 illustrate a representative respiratory care assembly 100 incorporating the novel clamping assembly 10 discussed above. Referring to FIGS. 3 and 4, the treatment device is illustrated as a catheter assembly 30 having a catheter tube 34 slidable within a sleeve 36. The distal end of the sleeve 36 is placed around the cylindrical portion 84 of the proximal member base 62 and the distal ring 38 is press-fitted onto the cylindrical portion 84 to secure the sleeve 36 relative to the clamping assembly 10. A proximal ring 40 is press-fitted onto an adaptor 44 and secures the proximal end of the sleeve 36 relative to the adaptor 44. A bushing 42 may be disposed around the proximal end of the catheter tube 34. The adaptor 44 is, in turn, connected to or formed integral with a proximal connector 46. The connector 46 is, in turn, connected to an air or oxygen source, suction source, lavage solution source, etc., depending on the particular medical procedure to be performed. For example, the catheter assembly 30 illustrated in FIGS. 3 and 4 is particularly suited for a gas insufflation procedure to oxygenate a patient's lungs. The connector 46 is connectable with an oxygen source for supplying oxygen through the catheter tube 34. The clinician advances the distal end of the catheter tube through the clamping assembly 10 until it is at the desired position at the cornea of the lung and then secures the catheter tube in position by actuating the clamping assembly 10 as described above. Oxygen is then supplied through the catheter tube directly into the patient's lungs.

In the embodiment illustrated in FIG. 5, the respiratory care assembly 100 includes a suction catheter assembly 30. In this embodiment, a suction valve 56 is at the proximal end of the catheter assembly and is in turn connected to a suction source. The configuration of the suction valve 56 is not particularly important to the present invention.

As mentioned, the distal member 12 is connectable to the patient's artificial airway. In the embodiment of FIG. 5, this connection is made through a manifold 50 that also simultaneously provides for ventilation of the patient with a conventional ventilator system 52 and ventilation lines 54. In this manner, the catheter assembly 30 can be connected or disconnected from the manifold 50 without interrupting ventilation to the patient. It should be appreciated that the arrangement of FIG. 5 is presented for illustrative purposes only and that the present invention is not limited to any particular type of system or device for connection to the patient's artificial airway.

It may be desired to form some or all of the components of the present invention out of clear or translucent materials such that a visual inspection of the components or the ongoing medical procedure is possible. For example, this would allow the clinician to monitor the color and consistency of mucous and secretions in a aspiration procedure.

It should also be understood that the components described herein may be formed of a variety of materials and from a variety of manufacturing processes. In some embodiments, the components of the present invention may be injection molded from a medical grade synthetic resinous material, such as a acrylic, flexible PVCS, modified polypropylene, or similar substances.

It should be appreciated by those skilled in the art that various modifications and variations can be made in the present invention without departing from the scope and spirit of the invention. It is intended that the present invention include such modifications and variations as come within the scope of the appended claims and their equivalents.

What is claimed is:

1. A clamping assembly for use with a respiratory care medical treatment device, said assembly comprising:

a proximal member, said proximal member being at least partially rotatable;

a distal member connected to said proximal member, said proximal member and said distal member being axially movable relative to each other;

a channel defined through said proximal and distal members, said channel configured for receipt of a medical treatment device passing therethrough;

a clamping member operatively configured between said proximal and distal members and defining at least a portion of said channel, said clamping member having an un-clamped configuration wherein said medical treatment device is slidable through said clamping member and channel, and a clamping configuration wherein said clamping member clamps upon and prevents axial movement of said medical treatment device through said channel, said proximal member rotating to engage and move said clamping member from said un-clamped configuration to said clamping configuration, wherein all of said clamping member is positioned proximally to said distal member; and wherein said clamping member is actuated by relative axial movement between said proximal and distal members.

2. The assembly as in claim 1, wherein said proximal member and said distal member are rotatable relative to each other, at least one of said proximal member and said distal members further comprising a gripping member axially spaced from a point of connection between said proximal and distal members.

3. The assembly as in claim 2, wherein said proximal member is rotatable relative to said distal member, and said gripping member comprises a grip ring configured on and defining a maximum outer diameter of said proximal member.

4. The assembly as in claim 1, wherein said proximal member and said distal member are threaddedly engaged.

5. The assembly as in claim 4, wherein said distal member is stationary and said proximal member is threaddedly engaged with and axially movable relative to said distal member, said clamping device comprising a compressible annular sleeve having an inner diameter that reduces upon said annular sleeve being compressed by axial advancement of said proximal member towards said distal member thereby causing said annular sleeve to clamp upon a medical treatment member disposed therethrough.

6. The assembly as in claim 1, wherein said clamping device comprises a compressible annular sleeve having opposite ends in contact with said proximal and distal members respectively, said annular sleeve disposed within a fixed diameter axially extending recess defined by one of said proximal and distal members such that relative axial movement between said proximal and distal members causes axial compression of said annual sleeve within said recess.

7. The assembly as in claim 6, wherein said proximal member is threadedly engaged with and axially advanceable towards said distal member, said proximal member defining said axially extending recess and said distal member comprising an axially extending protrusion extending into said recess and in contact with a distal end of said annular sleeve.

8. The assembly as in claim 1, wherein said proximal member further comprises a proximal tip configured for connection with a distal end of said medical treatment device.

9. The assembly as in claim 8, wherein said medical treatment device comprises a catheter assembly having a catheter tube slidable through said channel.

10. The assembly as in claim 1, wherein said distal member comprises a distal mating member configured for connection with a patient's artificial airway.

11. The assembly as in claim 10, wherein said mating member comprises a distally extending member sized for insertion into a receiving port of an artificial airway manifold.

12. A clamping assembly for use with a respiratory care medical treatment device, said assembly comprising:
   a first distal member and a second proximal member, at least one of said first and second members moveable relative to said other respective member, said second member being at least partially rotatable;
   an axial channel defined through said first and second members for sliding receipt of a respiratory care catheter tube therethrough;
   a clamping member disposed in-line with said first and second members, said clamping member having an un-clamped configuration wherein said catheter tube is slidable through said channel, and a clamping position wherein said clamping member clamps upon and prevents axial movement of said catheter tube relative to said channel, said second member rotating to engage and move said clamping member from said un-clamped configuration to said clamping position, wherein all of said clamping member is positioned proximally to said first distal member; and
   wherein said clamping member is actuated by relative movement between said first and second members.

13. The assembly as in claim 12, wherein said first and second members are axially moveable relative to each other.

14. The assembly as in claim 13, wherein said first and second members are threadedly engaged.

15. The assembly as in claim 12, wherein said clamping member comprises a compressible annular sleeve member having opposite axial ends in contact with said first and second members respectively, said annular sleeve member defining at least a portion of said axial channel; and
   wherein upon relative axial movement of said first and second members, said annular sleeve is compressed axially and radially inwardly and thereby clamps upon said catheter tube disposed therethrough, and upon opposite axial movement of first and second members, said annular sleeve releases said catheter tube.

16. The assembly as in claim 12, wherein said first and second members further comprise connection members at respective ends thereof so that said assembly is connectable in-line in a respiratory system.

17. A respiratory care assembly, comprising:
   a catheter assembly having a catheter tube configured for insertion through a patient's artificial airway;
   a clamping assembly for connecting said catheter assembly to the patient's artificial airway, said clamping assembly further comprising:
   a proximal member axially aligned with a distal member, said proximal member and said distal member being movable relative to each other, said proximal member being at least partially rotatable;
   a channel defined through said proximal and distal members, said catheter tube slidable through said channel for insertion into the patient's artificial airway;
   a clamping member disposed in-line with said proximal and distal members, said clamping member having an un-clamped configuration wherein said catheter tube is slidable through said channel, and a clamping position wherein said clamping member clamps upon and prevents axial movement of said catheter tube relative to said channel, said proximal member rotating to engage and move said clamping member from said un-clamped configuration to said clamping position, wherein all of said clamping member is positioned proximallly to said distal member; and
   wherein said clamping member is actuated by relative movement between said proximal and distal members.

18. The respiratory care assembly as in claim 17, wherein said proximal and distal members are axially moveable relative to each other and said clamping member comprises a compressible annular sleeve member having opposite axial ends in contact with said proximal and distal members respectively, said annular sleeve member defining at least a portion of said channel; and
   wherein upon relative axial movement of said proximal and distal members, said annular sleeve is compressed axially and radially inwardly and thereby clamps upon said catheter tube disposed therethrough.

19. The respiratory care assembly as in claim 19, wherein said proximal and distal members are threadedly engaged.

20. The respiratory care assembly as in claim 19, wherein said distal member is stationary and comprises a distal connecting member configured for connecting said clamping assembly to the patient's artificial airway.

21. The respiratory care assembly as in claim 19, wherein said proximal member rotates and threadedly advances relative to said distal member, said proximal member further comprising a proximal connecting member configured for connection with a distal end of said catheter assembly.

22. The respiratory care assembly as in claim 21, wherein said proximal member further comprises a grip ring configured thereon.

23. The respiratory care assembly as in claim 18, wherein said annular sleeve is disposed within a fixed diameter axially extending recess defined by one of said proximal and distal members.

* * * * *

UNITED STATES PATENT AND TRADEMARK OFFICE
CERTIFICATE OF CORRECTION

PATENT NO. : 6,688,306 B1
DATED : February 10, 2004
INVENTOR(S) : David M. Cise and Steven M. Wood It is certified that error appears in the above-identified patent and that said Letters Patent is hereby corrected as shown below:

Column 10,
Line 41, "claim 19" should read -- claim 18 --.

Signed and Sealed this

Twenty-first Day of September, 2004

JON W. DUDAS
*Director of the United States Patent and Trademark Office*